United States Patent
Fickel

(10) Patent No.: US 12,252,466 B2
(45) Date of Patent: Mar. 18, 2025

(54) ISOOCTANE PRODUCTION FROM FIELD BUTANE

(71) Applicant: SABIC Global Technologies B.V., Bergen op Zoom (NL)

(72) Inventor: Dustin Fickel, Sugar Land, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 107 days.

(21) Appl. No.: 18/038,169

(22) PCT Filed: Sep. 16, 2021

(86) PCT No.: PCT/US2021/050576
§ 371 (c)(1),
(2) Date: May 22, 2023

(87) PCT Pub. No.: WO2022/119614
PCT Pub. Date: Jun. 9, 2022

(65) Prior Publication Data
US 2023/0406788 A1    Dec. 21, 2023

Related U.S. Application Data

(60) Provisional application No. 63/121,250, filed on Dec. 4, 2020.

(51) Int. Cl.
*C07C 5/03*    (2006.01)
(52) U.S. Cl.
CPC .......... *C07C 5/03* (2013.01); *C07C 2529/44* (2013.01)

(58) Field of Classification Search
CPC ........ C07C 5/03; C07C 2529/44; C07C 2/74; C07C 4/06; C07C 2/76
See application file for complete search history.

(56) References Cited

U.S. PATENT DOCUMENTS

| 8,188,327 | B1 | 5/2012 | Bakshi |
| 2005/0080305 | A1 | 4/2005 | Kahn |
| 2016/0237004 | A1* | 8/2016 | Wang ................. B01J 29/22 |

FOREIGN PATENT DOCUMENTS

| WO | 0151435 A1 | 7/2001 |
| WO | 03066550 A1 | 8/2003 |
| WO | 20220119614 A1 | 6/2022 |

OTHER PUBLICATIONS

Filing Receipt, Specification and Drawings for U.S. Appl. No. 63/121,250 entitled "Isooctane Production from Field Butane," filed Dec. 4, 2020, 42 pages.

(Continued)

*Primary Examiner* — Ali Z Fadhel
(74) *Attorney, Agent, or Firm* — Norton Rose Fulbright US LLP

(57) ABSTRACT

A process for producing isooctane by introducing a butane feed stream (containing n-butane, i-butane) and hydrogen into a catalytic hydrogenolysis reactor to produce a hydrogenolysis product stream; separating the hydrogenolysis product stream into a butane stream (i-butane, optionally n-butane); feeding the butane stream to a catalytic dehydrogenation reactor to produce a dehydrogenation product stream comprising saturated and unsaturated four-carbon hydrocarbons; and feeding the dehydrogenation product stream to an oligomerization unit to produce isooctene and dehydrogenating the isooctene to produce isooctane.

21 Claims, 2 Drawing Sheets

(56) References Cited

OTHER PUBLICATIONS

Foreign Communication from Related Application—International Preliminary Report on Patentability, International Application No. PCT/US2021/050576, dated Jan. 12, 2022, 7 pages.
Foreign Communication from Related Application—International Search Report and Written Opinion of the International Searching Authority, International Application No. PCT/US2021/050576, dated Jan. 12, 2022, 7 pages.

\* cited by examiner

ISOOCTANE PRODUCTION FROM FIELD BUTANE

TECHNICAL FIELD

The present disclosure relates to methods of producing isooctane, more specifically methods of producing isooctane integrated with butane hydrogenolysis.

BACKGROUND

Isooctane is a chemical compound that is used as a fuel additive for gasoline (e.g., octane rating enhancer), and as a solvent. The conventional process for isooctane production uses butane-containing feedstreams from petroleum refining operations and includes the steps of dimerization of isobutylene, dimer separation, and hydrogenation. It would be beneficial to have an alternative route to this valuable chemical compound using field-grade butane. Such a route can start with a field-grade butane stream containing both n-butane and i-butane, wherein the field-grade butane stream is subjected to isomerization for conversion of n-butane to i-butane. However, such conversion is not complete, and a separation step is required after the isomerization to separate the isomerization product stream into an i-butane-rich stream and an n-butane-rich stream. The i-butane-rich stream can be sent to dehydrogenation to produce isobutylene, which can be used as discussed to produce isooctane. The isomerization and separation steps are capital and energy intensive. Thus, there is an ongoing need for the development of improved processes for the production of isooctane starting from a field-grade butane stream and for an alternative method to produce isooctane from unconventional feedstreams.

SUMMARY OF THE INVENTION

In some aspects of the invention, there is process comprising: (a) introducing a butane feed stream and hydrogen to a hydrogenolysis reactor to produce a hydrogenolysis product stream, wherein the hydrogenolysis reactor comprises a hydrogenolysis catalyst, wherein the butane feed stream comprises n-butane and i-butane, wherein said catalyst having higher selectivity towards hydrogenolysis of n-butane compared to hydrogenolysis of i-butane, wherein the hydrogenolysis product stream comprises hydrogen, methane, ethane, propane, i-butane, and n-butane, and further wherein said hydrogenolysis product stream has a higher i-butane:n-butane ratio than the butane feed stream; (b) separating at least a portion of the hydrogenolysis product stream in a first separation unit into a first hydrogen-containing stream, a stream rich in methane, ethane and propane, and a butane stream, wherein the butane stream comprises i-butane and n-butane; (c) feeding at least a portion of the butane stream to a dehydrogenation reactor to produce a dehydrogenation product stream, wherein the dehydrogenation reactor comprises a dehydrogenation catalyst, and wherein the dehydrogenation product stream comprises hydrogen, i-butane, isobutylene, n-butane, 1-butene, and 2-butene, (d) feeding at least a portion of the dehydrogenation product stream to an oligomerization unit to produce a product stream comprising isooctane; and (e) feeding at least a portion of the product stream comprising isooctene to a hydrogenation unit to produce isoocatane.

In various embodiments, n-butane is present in the butane feed stream in an amount of equal to or greater than about 50 mol %. The process may further comprise the step of recycling at least a portion of the first hydrogen-containing stream to the hydrogenolysis reactor. In various embodiments, the portion of the dehydrogenation product stream comprises the dehydrogenation product stream from step (c) after the removal of at least a portion of the hydrogen to form a second hydrogen-containing stream. In some instances, the process may further comprise the step of recycling at least a portion of the second hydrogen-containing stream to the hydrogenolysis reactor. Some non-limiting example conditions of the process include those wherein the hydrogenolysis reactor is characterized by a temperature of from about 200° C. to about 350° C.; a pressure of from about 0 psig to about 300 psig; a hydrocarbon-based weight hourly space velocity (WHSV) of from about 0.1 h$^{-1}$ to about 15 h$^{-1}$; and a hydrogen to C4 hydrocarbons molar ratio of from about 1:1 to about 10:1. In some examples of the inventive process, the hydrogenolysis catalyst comprises a hydrogenolysis monometallic supported catalyst and/or a hydrogenolysis bimetallic supported catalyst; wherein the hydrogenolysis monometallic supported catalyst comprises a zeolite-supported monometallic catalyst and/or an alumina-supported monometallic catalyst; wherein the hydrogenolysis bimetallic supported catalyst comprises a zeolite-supported bimetallic catalyst and/or an alumina-supported bimetallic catalyst; wherein the hydrogenolysis bimetallic supported catalyst comprises a first metal and a second metal, wherein the first metal and the second metal are different; wherein the hydrogenolysis monometallic supported catalyst comprises a third metal; wherein the third metal is the same as or different from the first metal and/or the second metal; wherein the first metal, the second metal, and the third metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co); wherein the support comprises alumina and/or a zeolite; wherein the zeolite is selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof; and wherein the support optionally comprises a binder comprising alumina, titania, silica, or combinations thereof. Preferably, the hydrogenolysis catalyst comprises Pt and Ir supported on ZSM-5.9. In some cases, the inventive process further comprises recycling at least a portion of the dehydrogenation product stream to the dehydrogenation reactor.

In various embodiments, the aforementioned step (b) of separating at least a portion of the hydrogenolysis product stream in a first separation unit further comprises separating at least a portion of the n-butane from the hydrogenolysis product stream. In various other embodiments, the process further comprises recycling at least a portion of the separated n-butane to the hydrogenolysis reactor.

In various embodiments, the hydrogenolysis reactor is characterized by an i-butane conversion of less than about 25%. Also in various embodiments, the hydrogenolysis reactor is characterized by a n-butane conversion of equal to or greater than about 70%.

In some non-limiting examples, the process further comprises feeding at least a portion of the stream rich in methane, ethane and propane to a gas steam cracker furnace to produce a steam cracker product stream, wherein the steam cracker product stream comprises ethylene and propylene. The process may have an ethane to propane weight ratio in the stream rich in methane, ethane and propane that is equal to or greater than about 2:1.

In some aspects of the invention, there is a process for producing isooctane comprising: (a) introducing a butane feed stream and hydrogen to a hydrogenolysis reactor to produce a hydrogenolysis product stream, wherein the hydrogenolysis reactor comprises a hydrogenolysis bimetallic supported catalyst, wherein the hydrogenolysis bimetallic supported catalyst comprises Pt and Ir supported on ZSM-5, wherein the hydrogenolysis reactor is characterized by a temperature of less than about 350° C., wherein the hydrogenolysis reactor is characterized by an i-butane conversion of less than about 25%, wherein the butane feed stream comprises n-butane and i-butane, wherein the butane feed stream is characterized by a mole ratio of n-butane to i-butane of equal to or greater than about 1:1, and wherein the hydrogenolysis product stream comprises hydrogen, methane, ethane, propane, i-butane, and n-butane; (b) separating at least a portion of the hydrogenolysis product stream in a first separation unit into a first hydrogen-containing stream, a stream rich in methane, ethane and propane, and a first i-butane stream; (c) feeding at least a portion of the first i-butane stream to a dehydrogenation reactor to produce a dehydrogenation product stream, wherein the dehydrogenation reactor comprises a dehydrogenation catalyst, and wherein the dehydrogenation product stream comprises hydrogen, i-butane, and isobutylene; (d) separating at least a portion of the dehydrogenation product stream in a second separation unit into a second hydrogen-containing stream, a second i-butane stream, and an isobutylene stream; and (e) feeding at least a portion of the isobutylene stream and hydrogen to an oligomerization unit to produce a isooctane-containing stream.

In some examples, the process further comprises the step of feeding at least a portion of the stream rich in methane, ethane and propane to a gas steam cracker furnace to produce a steam cracker product stream, wherein the steam cracker product stream comprises olefins. Preferably, the steam cracker product stream comprises ethylene and propylene in a weight ratio of ethylene to propylene of equal to or greater than about 2:1.

In various embodiments, the process further comprises recycling at least a portion of the first hydrogen-containing stream and/or at least a portion of the second hydrogen-containing stream to the hydrogenolysis reactor. In some examples, the process further comprises the step of recycling at least a portion of the second i-butane stream to the dehydrogenation reactor.

BRIEF DESCRIPTION OF THE DRAWINGS

For a detailed description of the preferred aspects of the disclosed methods, reference will now be made to the accompanying drawing in which.

DETAILED DESCRIPTION

Figure 1:
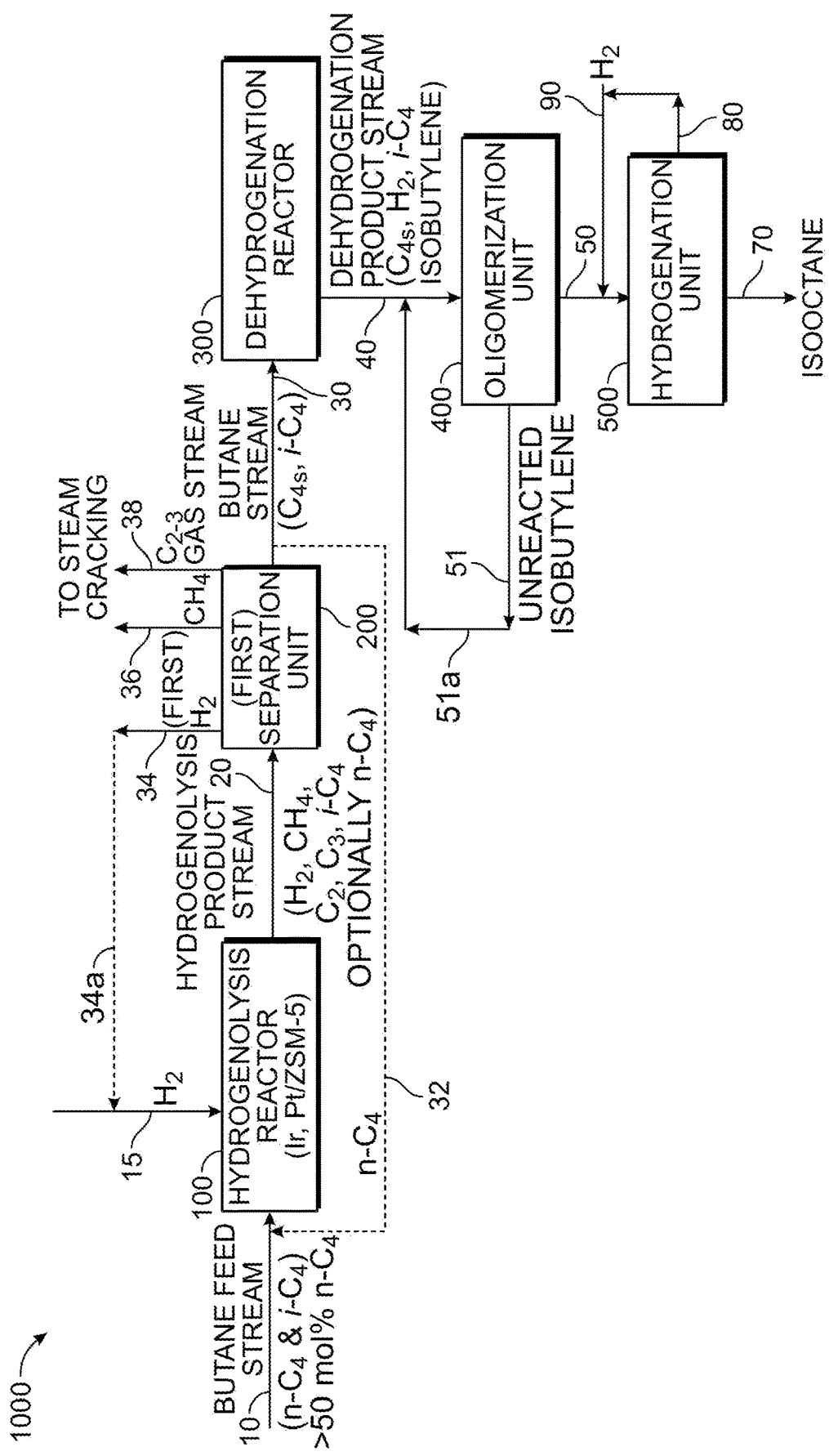
FIG. 1 displays a configuration of an isooctane production system.

Disclosed herein are processes integrating a butane hydrogenolysis reactor with a dehydrogenation reactor, and an oligomerization unit for the production of isooctane, wherein a feed stream to the process comprises a mixed butane stream (e.g., field-grade butane). Generally, field-grade butane streams (also sometimes referred to as "field butane") comprise a mixture of n-butane and i-butane; for example from about 60 mol % to about 75 mol % n-butane, and from about 25 mol % to about 40 mol % i-butane. By using a hydrogenolysis catalyst in a hydrogenolysis reactor, field-grade butane streams can be reactively separated via selectively reacting the n-butane from the field-grade butane streams. A hydrogenolysis reactor can convert the n-butane to a gaseous stream of methane, ethane, and propane (predominately ethane; and specifically more ethane than a comparative hydrocracking reactor cracking the same amount of n-butane). Hydrogen can be co-fed with the field-grade butane stream to the hydrogenolysis reactor. The hydrogenolysis catalyst can comprise a variety of monometallic catalysts. Non-limiting examples include Pt or Ir supported on alumina, and/or Pt or Ir supported on ZSM-5 and/or bimetallic catalysts such as Pt and Ir supported on alumina, and/or Pt and Ir supported on ZSM-5.

Generally, i-butane is minimally converted in the hydrogenolysis reactor (e.g., the hydrogenolysis reactor can be characterized by an i-butane conversion of less than about 25%). This minimal conversion preserves the i-butanes for further uses where it is particularly useful. The hydrogenolysis reaction can be run with operational parameters (e.g., catalyst, pressure, temperature, flow rate, etc.) effective for limiting (e.g., minimizing, reducing, etc.) i-butane conversion, thus resulting in high ethane selectivity. Without wishing to be limited by theory, when i-butane is converted, 1 mole of i-butane generally converts to 1 mole of methane and 1 mole of propane (i.e., no ethane); and by avoiding or minimizing i-butane conversion, the overall ethane selectivity can be increased. Further, n-butane is converted to a much greater extent than is i-butane in the hydrogenolysis reactor (i.e., n-butane conversion is maximized in the hydrogenolysis reactor); for example, the hydrogenolysis reactor can be characterized by an n-butane conversion of greater than about 90%. The hydrogenolysis reaction can be run with operational parameters effective for maximizing (e.g., enhancing, increasing, etc.) n-butane conversion, thus resulting in high ethane selectivity. Without wishing to be limited by theory, when n-butane is converted, 1 mole of n-butane generally converts to 2 moles of ethane; and by maximizing n-butane conversion, the overall ethane selectivity can be increased. The process for producing olefins as disclosed herein can maximize the production of ethane in the hydrogenolysis reaction. As will be appreciated by one of skill in the art, and with the help of this disclosure, as the conversion of n-butane undesirably lessens in the hydrogenolysis reactor and/or as more i-butane is undesirably converted in the hydrogenolysis reactor, the amount of ethane produced and/or the ethane selectivity, respectively, decrease in the hydrogenolysis reactor.

The i-butane recovered from the hydrogenolysis reactor can be fed to a dehydrogenation reactor, wherein i-butane can be converted to a mixture of isobutylene and hydrogen. The product stream will also comprise ethane and propane. At least a portion of produced hydrogen can be directed back to the hydrogenolysis reactor. The ethane and/or propane produced in the hydrogenolysis reactor can be further sent to a steam cracking furnace for ethylene and/or propylene production. The isobutylene can dimerized to produce isooctane, a valuable product. In this way, field-grade butane streams can be optimally utilized for conversion to valuable products.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced items. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "various aspects", "some aspects,", "an embodiment", "another embodiment", "other embodiments", "various embodiments", "some embodiments", and so forth, means that a particular element (e.g., feature, structure, property, and/or characteristic) described in connection with the aspect or embodiment is included in at least an aspect or embodiment described herein, and may or may not be present in other aspects or embodiments. In addition, it is to be understood that the described element(s) can be combined in any suitable manner in the various aspects or embodiments.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

As used herein, "isooctane" means the eight-carbon hydrocarbon 2,2,4-trimethylpentane. As used herein "n-butane" (normal butane) has its commonly known meeting and is the straight-chain, unbranched, four-carbon hydrocarbon having the formula $CH_3CH_2CH_2CH_3$. As used herein "i-butane" (isobutane) has its commonly known meeting and is the branched-chain, four-carbon hydrocarbon having the formula $(CH_3)_2CHCH_3$. As used herein "isobutylene" (also known as isobutene and 2-methylpropene) has its commonly known meeting and is the branched-chain, monounsaturated four-carbon hydrocarbon having the formula $(CH_3)_2CH=CH_2$.

Referring to FIG. 1, an isooctane production system 1000 is disclosed. The isooctane production system 1000 generally comprises a hydrogenolysis reactor 100; a first separation unit 200; a dehydrogenation reactor 300; an oligomerization unit 400; and a hydrogenation unit 500.

Figure 2:
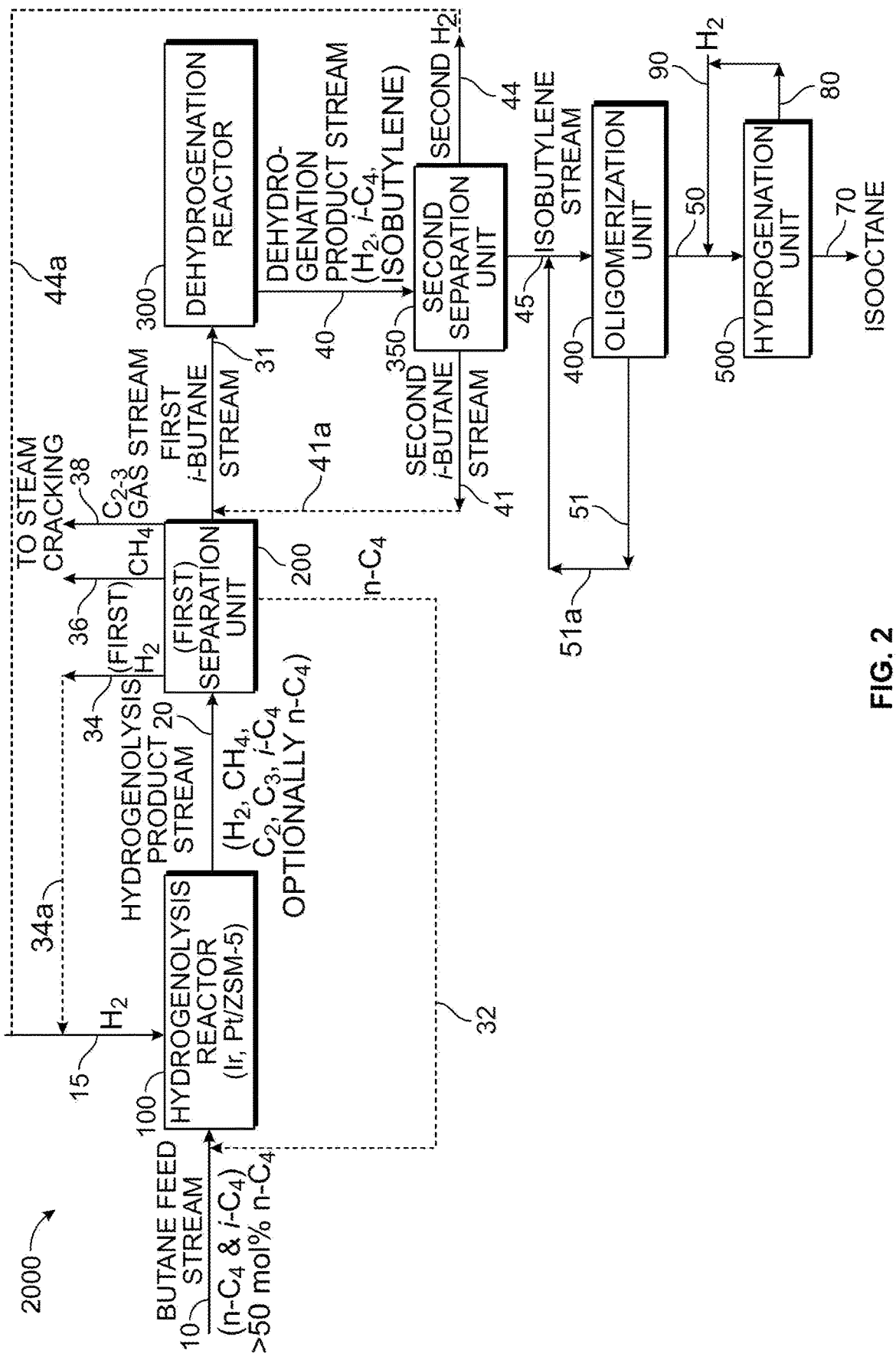
FIG. 2 displays another configuration of an isooctane production system.

Referring to FIG. 2, an isooctane production system 2000 is disclosed. The isooctane production system 2000 generally comprises a hydrogenolysis reactor 100; a first separation unit 200; a dehydrogenation reactor 300; a second separation unit 350; an oligomerization unit 400; and a hydrogenation unit 500. As will be appreciated by one of skill in the art, and with the help of this disclosure, isooctane production system components shown in FIGS. 1, and 2 can be in fluid communication with each other (as represented by the connecting lines indicating a direction of fluid flow) through any suitable conduits (e.g., pipes, streams, etc.). Common reference numerals refer to common components present in one or more of the Figures, and the description of a particular component is generally applicable across respective Figures wherein the component is present, except as otherwise indicated herein.

In an aspect, the process for producing isooctane as disclosed herein can comprise introducing a butane feed stream 10 and hydrogen 15 to the hydrogenolysis reactor 100 to produce a hydrogenolysis product stream 20, wherein the hydrogenolysis reactor 100 comprises a hydrogenolysis catalyst, wherein the butane feed stream 10 comprises n-butane and i-butane, and wherein the hydrogenolysis product stream 20 comprises hydrogen, methane, ethane, propane, i-butane, and optionally n-butane. In some aspects, the hydrogenolysis product stream 20 can further comprise some impurities, such as $C_{5+}$ hydrocarbons. In some aspects, the hydrogenolysis product stream 20 is substantially free of n-butane.

Generally, hydrogenolysis refers to a chemical reaction whereby a carbon-carbon or carbon-heteroatom single bond is cleaved or undergoes "lysis" by hydrogen, usually at relatively low temperatures (e.g., less than about 330° C.). For purposes of the disclosure herein, the term "selective hydrogenolysis" refers to a hydrogenolysis process wherein two or more different hydrocarbons (e.g., first hydrocarbon, second hydrocarbon; n-butane, i-butane) are subjected to a hydrogenolysis reaction, and wherein at least one hydrocarbon (e.g., first hydrocarbon; n-butane) undergoes hydrogenolysis, and wherein at least one hydrocarbon (e.g., second hydrocarbon; i-butane) is resistant to hydrogenolysis (e.g., has a low conversion in a hydrogenolysis reaction, such as less than about 25% conversion), under the same given set of reaction conditions (e.g., catalyst, pressure, temperature, flow rate, etc.). Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. Without wishing to be limited by theory, the hydrogenolysis reaction rate of the first hydrocarbon (e.g., n-butane) is greater than the hydrogenolysis reaction rate of the second hydrocarbon (e.g., i-butane), thereby allowing the separation (e.g., reactive separation) of n-butane and i-butane by consuming the n-butane in the hydrogenolysis reaction and recovering the unreacted i-butane. As will be appreciated by one of skill in the art, and with the help of this disclosure, the selective hydrogenolysis of n-butane from a butane feed stream (e.g., butane feed stream 10) comprising n-butane and i-butane provides for the reactive separation of n-butane from i-butane.

In an aspect, the butane feed stream 10 can comprise n-butane and i-butane. In some aspects, the butane feed stream 10 can comprise n-butane in an amount of equal to or greater than about 5 mol %, alternatively equal to or greater than about 10 mol %, alternatively equal to or greater than about 20 mol %, alternatively equal to or greater than about 30 mol %, alternatively equal to or greater than about 40 mol %, alternatively equal to or greater than about 50 mol %, alternatively equal to or greater than about 60 mol %, alternatively equal to or greater than about 70 mol %, alternatively equal to or greater than about 80 mol %, or alternatively equal to or greater than about 90 mol %.

The butane feed stream 10 can comprise i-butane in an amount of equal to or greater than about 5 mol %, alternatively equal to or greater than about 10 mol %, alternatively equal to or greater than about 20 mol %, alternatively equal to or greater than about 30 mol %, alternatively equal to or greater than about 40 mol %, alternatively equal to or greater than about 50 mol %, alternatively equal to or greater than about 60 mol %, alternatively equal to or greater than about 70 mol %, alternatively equal to or greater than about 80 mol %, or alternatively equal to or greater than about 90 mol %.

In an aspect, the butane feed stream 10 can be characterized by a mole ratio of n-butane to i-butane of equal to or greater than about 0.05:1, alternatively equal to or greater than about 0.1:1, alternatively equal to or greater than about 0.25:1, alternatively equal to or greater than about 0.5:1, alternatively equal to or greater than about 1:1, alternatively equal to or greater than about 2:1, alternatively equal to or greater than about 2.5:1, alternatively equal to or greater than about 5:1, alternatively equal to or greater than about 7.5:1, alternatively equal to or greater than about 10:1, alternatively from about 0.05:1 to about 10:1, alternatively from about 0.1:1 to about 7.5:1, alternatively from about 0.25:1 to about 5:1, or alternatively from about 0.5:1 to about 2.5:1.

In an aspect, the butane feed stream 10 can comprise n-butane in an amount of equal to or greater than about 50 mol %. In such aspect, the butane feed stream 10 can comprise i-butane in an amount of less than about 50 mol %.

In an aspect, the butane feed stream 10 can comprise field grade-butane (e.g., mixed butane). Field-grade butane is generally produced by natural gas processing and/or oil refining. Field-grade butane can comprise from about 50 mol % to about 80 mol %, alternatively from about 55 mol % to about 80 mol %, or alternatively from about 60 mol % to about 75 mol % n-butane; and from about 20 mol % to about 50 mol %, alternatively from about 20 mol % to about 45 mol %, or alternatively from about 25 mol % to about 40 mol % i-butane. Field-grade butane can further comprise from about 0 mol % to about 5 mol % propane and/or pentanes. In some aspects, the field-grade butane can be characterized by a mole ratio of n-butane to i-butane of from about 1:1 to about 4:1, alternatively from about 1.2:1 to about 4:1, or alternatively from about 1.5:1 to about 3:1.

In an aspect, the hydrogenolysis reactor 100 can comprise a fixed bed reactor, a radial flow reactor, a multi-layered bed reactor, a continuous flow reactor, an adiabatic reactor, an isothermal reactor, and the like, or combinations thereof.

In an aspect, the hydrogenolysis reactor 100 can be characterized by a temperature (e.g., hydrogenolysis temperature) of from about 200° C. to about 330° C., alternatively from about 250° C. to about 325° C., or alternatively from about 280° C. to about 310° C. As will be appreciated by one of skill in the art, and with the help of this disclosure, temperatures below 330° C. are conducive to selective hydrogenolysis. By contrast to hydrogenolysis, hydrocracking refers to a process that rearranges and breaks hydrocarbon chains, as well as adds hydrogen to unsaturated hydrocarbons to produce saturated hydrocarbons, at relatively high temperatures (e.g., greater than about 330° C.).

As will be appreciated by one of skill in the art, and with the help of this disclosure, and without wishing to be limited by theory, given the same feed stream, hydrogenolysis and hydrocracking will produce a different product distribution, owing to different reaction mechanisms, which can activate or inhibit different components of a given catalyst. For example, relatively high temperatures (e.g., hydrocracking temperatures, such as greater than about 400° C.) can inactivate one of the metals of a hydrogenolysis catalyst (e.g., a metal of a hydrogenolysis bimetallic supported catalyst, such as Ir), thereby promoting cracking and hydrogenation of all components of the feed stream (e.g., n-butane and i-butane) in the presence of the partially inactivated hydrogenolysis catalyst. Further, as will be appreciated by one of skill in the art, and with the help of this disclosure, and without wishing to be limited by theory, relatively high temperatures (e.g., hydrocracking temperatures, such as greater than about 400° C.) are generally needed to get over the activation energy to begin cracking. Furthermore, as will be appreciated by one of skill in the art, and with the help of this disclosure, and without wishing to be limited by theory, the branched i-butane is a more stable molecule than the linear n-butane, and as such higher temperatures (e.g., greater than about 400° C.) are generally necessary to activate i-butane in a cracking process.

In an aspect, hydrogenolysis of the butane feed stream 10 at relatively low temperatures (e.g., less than about 330° C.) can increase an amount of ethane in the hydrogenolysis product stream 20, as compared to an amount of ethane in a product stream obtained from an otherwise similar process that would be run at relatively high temperatures (e.g., greater than about 330° C.).

As will be appreciated by one of skill in the art, and with the help of this disclosure, hydrocracking of a butane feed stream at relatively high temperatures (e.g., greater than about 330° C.) can increase an amount of propane and/or methane in the product stream, as compared to an amount of propane and/or methane, respectively in a product stream obtained from an otherwise similar process (e.g., hydrogenolysis process) that is run at relatively low temperatures (e.g., less than about 330° C.). Further, as will be appreciated by one of skill in the art, and with the help of this disclosure, and without wishing to be limited by theory, hydrocracking follows a different reaction mechanism or pathway as compared to hydrogenolysis, which leads to an increased amount of propane in hydrocracking as compared to hydrogenolysis.

The hydrogenolysis reactor 100 can be characterized by a pressure (e.g., hydrogenolysis pressure) of from about 0 psig to about 300 psig, alternatively from about 10 psig to about 300 psig, alternatively from about 20 psig to about 200 psig, alternatively from about 50 psig to about 150 psig, alternatively from about 75 psig to about 125 psig, or alternatively from about 90 psig to about 110 psig.

The hydrogenolysis reactor 100 can be characterized by a hydrocarbon-based weight hourly space velocity (WHSV) of from about 0.1 $h^{-1}$ to about 15 $h^{-1}$, alternatively from about 0.5 $h^{-1}$ to about 10 $h^{-1}$, or alternatively from about 1 $h^{-1}$ to about 5 $h^{-1}$. Generally, the WHSV refers to a mass of reagents (e.g., hydrocarbons) fed per hour divided by a mass of catalyst used in a particular reactor.

The hydrogenolysis reactor 100 can be characterized by a hydrogen to $C_4$ hydrocarbons molar ratio of from about 1:1 to about 10:1, alternatively from about 1.5:1 to about 7.5:1, or alternatively from about 2:1 to about 5:1.

In some aspects, the hydrogenolysis reactor 100 can be operated under an optimal set of operational parameters that result in substantially consuming all of the n-butane in the hydrogenolysis reactor 100, wherein the hydrogenolysis product stream 20 is substantially free of n-butane (and consequently butane stream 30 is substantially free of n-butane). As will be appreciated by one of skill in the art, and with the help of this disclosure, the reactor parameters are contributing in an interdependent manner to reaction rates (e.g., rates of consuming reactants, such as n-butane and i-butane); for example, reaction temperature (e.g., hydrogenolysis temperature) and WHSV contribute interdependently to the rate of reaction of n-butane and i-butane in the hydrogenolysis reactor (e.g., hydrogenolysis reactor 100). In an aspect, in order to substantially consume all of the n-butane in the hydrogenolysis reactor 100, the hydrogenolysis reactor 100 can be operated at (e.g., held at) a temperature of from about 280° C. to about 300° C. for the following parameters. For example, in order to substantially consume all of the n-butane in the hydrogenolysis reactor 100, the hydrogenolysis reactor 100 can be operated at a temperature of from about 280° C. to about 300° C., a WHSV of from about 0.1 $h^{-1}$ to about 5 $h^{-1}$, a pressure of from about 0 psig to about 100 psig, a hydrogen to $C_4$ hydrocarbons molar ratio of from about 2:1 to about 2.5:1; and in the presence of a hydrogenolysis bimetallic supported catalyst comprising Pt and Ir supported on ZSM-5, wherein Pt is present in a total amount of from about 0.2 wt. % to about 0.4 wt. %, or alternatively about 0.3 wt. %, based on the total weight of the hydrogenolysis bimetallic supported catalyst; wherein Ir is present in a total amount of from about 0.2 wt. % to about 0.4 wt. %, or alternatively about 0.3 wt. %, based on the total weight of the hydrogenolysis bimetallic supported catalyst; wherein Pt and Ir are present in a weight ratio of Pt to Ir of from about 0.8:1 to about 1.2:1, or alternatively about 1:1; and wherein the ZSM-5 is characterized by a weight ratio of silica to alumina ($SiO_2/Al_2O_3$) of from about 250 to about 300, or alternatively about 280.

In an aspect, the hydrogenolysis reactor 100 can comprise a hydrogenolysis catalyst. In some aspects, the hydrogenolysis catalyst can comprise a hydrogenolysis monometallic supported catalyst, such as a zeolite-supported monometallic catalyst and/or an alumina-supported monometallic catalyst. In other aspects, the hydrogenolysis catalyst can comprise a hydrogenolysis bimetallic supported catalyst, such as a zeolite-supported bimetallic catalyst and/or an alumina-supported bimetallic catalyst. In yet other aspects, the hydrogenolysis catalyst can comprise a hydrogenolysis monometallic supported catalyst and a hydrogenolysis bimetallic supported catalyst.

In some aspects, a hydrogenolysis bimetallic supported catalyst as disclosed herein can comprise a first metal, a second metal, and a support; wherein the first metal and the second metal are different. In other aspects, a hydrogenolysis monometallic supported catalyst as disclosed herein can comprise a third metal and a support. In some aspects, the third metal can be the same as the first metal or the second metal. In other aspects, the third metal can be the different from the first metal and/or the second metal.

In an aspect, the first metal, the second metal, and the third metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co).

In an aspect, the first metal, the second metal, and the third metal can each independently be one or more metals from Group 6 of the Periodic Table; one or more metals from Group 8 of the Periodic Table; one or more metals from Group 9 of the Periodic Table; one or more metals from Group 10 of the Periodic Table; or combinations thereof; wherein the first metal and the second metal are different; and wherein the third metal is the same as or different from the first metal and/or the second metal.

In some aspects, the first metal comprises Pt, and the second metal comprises Ir. In other aspects, the first metal comprises Pt, and the second metal comprises Rh. In yet other aspects, the first metal comprises Pt, and the second metal comprises Ir and Rh.

In some aspects, the third metal can comprise, Pt, Ir, or Rh.

In an aspect, the first metal and the second metal can be present in the hydrogenolysis bimetallic supported catalyst in a weight ratio of first metal to second metal of from about 0.1:1 to about 10:1, alternatively from about 0.5:1 to about 7:1, alternatively from about 1:1 to about 4:1, alternatively from about 0.3:1 to about 3:1, alternatively from about 0.5:1 to about 2:1, alternatively from about 0.7:1 to about 1.5:1, or alternatively from about 0.8:1 to about 1.2:1.

In an aspect, the first metal and the second metal can be present in the hydrogenolysis bimetallic supported catalyst in a total amount (i.e., first metal amount+second metal amount) of from about 0.1 wt. % to about 10 wt. %, alternatively from about 0.15 wt. % to about 5 wt. %, alternatively from about 0.2 wt. % to about 1 wt. %, alternatively from about 0.4 wt. % to about 0.8 wt. %, or alternatively from about 0.5 wt. % to about 0.7 wt. %, based on the total weight of the hydrogenolysis bimetallic supported catalyst.

In an aspect, the third metal can be present in the hydrogenolysis monometallic supported catalyst in a total amount of from about 0.1 wt. % to about 10 wt. %, alternatively from about 0.15 wt. % to about 5 wt. %, alternatively from about 0.2 wt. % to about 1 wt. %, alternatively from about 0.4 wt. % to about 0.8 wt. %, or alternatively from about 0.5 wt. % to about 0.7 wt. %, based on the total weight of the hydrogenolysis monometallic supported catalyst.

In an aspect, the support suitable for use in the hydrogenolysis catalyst of the current disclosure can comprise alumina, silica-alumina, and/or a zeolite, or any combination thereof.

In some aspects, the support suitable for use in the hydrogenolysis catalyst of the current disclosure can consist of or consist essentially of alumina and/or a zeolite. In other aspects, the support suitable for use in the hydrogenolysis catalyst of the current disclosure can comprise alumina and/or a zeolite, and a binder. Generally a binder can be used to improve mechanical properties of a support (e.g., improve resistance to attrition). Nonlimiting examples of binders suitable for use in the hydrogenolysis catalyst as disclosed herein include alumina, titania, silica, silica-alumina, and the like, or combinations thereof.

In some aspects, a hydrogenolysis catalyst as disclosed herein can comprise an alumina support. For purposes of the disclosure herein the term "alumina support(s)" includes any suitable type of alumina ($Al_2O_3$), such as alpha alumina, beta alumina, gamma alumina, eta alumina, theta alumina, amorphous alumina, and the like, or combinations thereof. The support may be, or include, a silica-alumina.

In some aspects, a hydrogenolysis catalyst as disclosed herein can comprise a zeolitic support. For purposes of the disclosure herein the term "zeolitic support(s)" includes zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof. Further, for purposes of the disclosure herein, zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof are referred to herein collectively as "zeolites."

The zeolitic support can comprise zeolites such as small pore zeolites, medium pore zeolites, large pore zeolites, or combinations thereof. Zeolites are inorganic crystalline solids having a framework structure with channels and cavities with characteristic pore geometry. Zeolites can be classified according to their pore openings. For example, small pore zeolites have 8 membered ring pore openings, which can be characterized by a pore size (e.g., diameter of the pore opening) of from 3 Å to 4.5 Å; medium pore zeolites have 10 membered ring pore openings, which can be characterized by a pore size (e.g., diameter of the pore opening) of from 4.5 Å to 6.0 Å; and large pore zeolites have 12 membered ring pore openings, which can be characterized by a pore size (e.g., diameter of the pore opening) of from 6.0 Å to 8.0 Å.

In some aspects, the zeolitic support can comprise one or more aluminosilicate zeolites containing $SiO_4$ and $AlO_4$ tetrahedra in their structure (e.g., framework structure). In other aspects, the zeolitic catalyst can comprise a zeolite-type material, such as silicoaluminophosphates (SAPOs) containing $PO_4$, $AlO_4$ and $SiO_4$ tetrahedra in the structure (e.g., framework structure); and/or aluminophosphates (AlPOs) containing $PO_4$, and $AlO_4$ tetrahedra in the structure (e.g., framework structure). The $SiO_4$, $AlO_4$ and/or $PO_4$ tetrahedra share oxygen atoms, wherein the framework structures have well defined channels and cavities (e.g., pores). These cavities may generally contain exchangeable cations, such as $H^+$, $Na^+$ and $K^+$. Without wishing to be limited by theory, in the zeolite framework structure or zeolite-type framework structure, Si or Al or P can be partially substituted by other tri-valent or tetra-valent elements, such as Ge, Ga, B, etc. Further, and without wishing to be limited by theory, in zeolites, Si or Al or P can also be partially substituted by one or more elements selected from the group consisting of titanium, nickel, copper, magnesium, tin, cobalt, iron, zinc, tungsten, vanadium, gallium, calcium, manganese, ruthenium and rhenium.

Without wishing to be limited by theory, zeolites are generally characterized by a certain acidity, owing to the presence of Brønsted acid sites and/or Lewis acid sites. In zeolites, a Brønsted acidic proton can be a hydrogen atom bonded to the oxygen atom that connects the tetrahedrally coordinated aluminum which forms the zeolite structural framework. The Lewis acid centers in zeolites can contain tri-coordinated aluminum sites, which are electron deficient sites exhibiting the ability to accept electrons during interactions with molecules. In some aspects, the zeolite suitable for use in the zeolitic support as disclosed herein can be treated to reduce its acidity, for example by titration with a basic salt containing $Na^+$ and/or $K^+$ cations (e.g., by impregnation, ion-exchange, etc.). As will be appreciated by one of skill in the art, and with the help of this disclosure, and without wishing to be limited by theory, acidic sites in a zeolite can promote isomerization of n-butane to i-butane. In some aspects, the zeolitic support can be characterized by low acidity and/or low aluminum content; e.g., the zeolitic support can be characterized by low Brønsted acidity. In some aspects, the zeolitic support can be characterized by substantially no acidity (i.e., zero acidity).

In some aspects, the zeolitic support can be characterized by a weight ratio of silica to alumina ($SiO_2/Al_2O_3$) of equal to or greater than about 100, alternatively equal to or greater than about 150, alternatively equal to or greater than about 200, alternatively equal to or greater than about 250, alternatively equal to or greater than about 275, alternatively equal to or greater than about 300, alternatively from about 100 to about 400, alternatively from about 200 to about 350, alternatively from about 250 to about 300, alternatively from about 275 to about 290, or alternatively about 280. In an aspect, the zeolitic support (e.g., ZSM-5) can be characterized by a weight ratio of silica to alumina ($SiO_2/Al_2O_3$) of 280. As will be appreciated by one of skill in the art, and with the help of this disclosure, and without wishing to be limited by theory, the acidity of a support decreases with increasing its weight ratio of silica to alumina ($SiO_2/Al_2O_3$).

In an aspect, the zeolitic support can comprise a zeolite, wherein the zeolite can be selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof.

In some aspects, a zeolitic support can comprise from about 70 wt. % to about 90 wt. %, alternatively from about 75 wt. % to about 85 wt. %, or alternatively about 80 wt. % zeolite; and from about 10 wt. % to about 30 wt. %, alternatively from about 15 wt. % to about 25 wt. %, or alternatively about 20 wt. % binder (e.g., alumina binder); based on the total weight of the zeolitic support.

In an aspect, the zeolitic support can be present in the hydrogenolysis bimetallic supported catalyst in an amount of from about 90 wt. % to about 99.9 wt. %, alternatively from about 95 wt. % to about 99.85 wt. %, or alternatively from about 99 wt. % to about 99.8 wt. %, based on the total weight of the hydrogenolysis bimetallic supported catalyst.

In an aspect, a hydrogenolysis bimetallic supported catalyst as disclosed herein can comprise a first metal, a second metal, and a zeolitic support; wherein the first metal comprises Pt, wherein the second metal comprises Ir, and wherein the zeolitic support comprises ZSM-5.

The hydrogenolysis bimetallic supported catalyst as disclosed herein can be prepared by any suitable methodology, for example as described in more detail in U.S. Provisional Patent Application No. 62/733,309, filed Sep. 19, 2018, which is incorporated by reference herein in its entirety.

In an aspect, the hydrogenolysis bimetallic supported catalyst as disclosed herein can be characterized by a selectivity to ethane of from about 60 mol % to about 90 mol %, alternatively from about 65 mol % to about 85 mol %, or alternatively from about 70 mol % to about 80 mol %. Generally, a selectivity to a desired product or products refers to how much desired carbon product was formed divided by the total carbon products formed, both desired and undesired. For purposes of the disclosure herein, the selectivity to a desired product is a % selectivity based on moles converted into the desired product.

In an aspect, the hydrogenolysis bimetallic supported catalyst as disclosed herein can be characterized by a selectivity to methane of less than about 20 mol %, alternatively less than about 15 mol %, or alternatively less than about 12.5 mol %.

In an aspect, the hydrogenolysis bimetallic supported catalyst as disclosed herein can be characterized by a selectivity to propane of less than about 15 mol %, alternatively less than about 12.5 mol %, or alternatively less than about 10 mol %.

In an aspect, the hydrogenolysis reactor 100 can be characterized by an i-butane conversion that is less than an n-butane conversion. As will be appreciated by one of skill in the art, and with the help of this disclosure, the conversion of reagents in hydrogenolysis is dependent on a variety of reactor conditions, such as flow rate, temperature, etc.

In an aspect, the hydrogenolysis reactor 100 can be characterized by an i-butane conversion of less than about 25%, alternatively less than about 20%, alternatively less than about 15%, alternatively less than about 10%, alternatively less than about 5%, alternatively less than about 1%, alternatively less than about 0.5%, alternatively less than about 0.1%, alternatively less than about 0.01%, or alternatively less than about 0.001%.

In an aspect, the hydrogenolysis reactor 100 can be characterized by a n-butane conversion of equal to or greater than about 75%, alternatively equal to or greater than about 80%, alternatively equal to or greater than about 85%, alternatively equal to or greater than about 90%, alternatively equal to or greater than about 95%, or alternatively equal to or greater than about 99%. In some aspects, the hydrogenolysis reactor 100 can be characterized by an n-butane conversion of 100%. In some aspects, substantially all of the n-butane introduced to the hydrogenolysis reactor 100 is converted; e.g., the hydrogenolysis product stream 20 is substantially free of n-butane.

In some aspects, the hydrogenolysis reactor 100 can be characterized by an i-butane conversion of less than about 25%, and by a n-butane conversion of equal to or greater than about 90%.

In an aspect, the process for producing isooctane as disclosed herein can comprise feeding at least a portion of the hydrogenolysis product stream 20 to the first separation unit 200 (as depicted in FIG. 1) to yield a butane stream 30, a first hydrogen-containing stream 34, an optional methane stream 36, and a $C_2$ to $C_3$ gas stream 38; wherein the $C_2$ to $C_3$ gas stream 38 comprises ethane and propane, and wherein the butane stream 30 comprises i-butane and optionally n-butane. In aspects where only a fairly low amount of methane is produced during hydrogenolysis (e.g., methane make is relatively low), methane could be separated along with the hydrogen, wherein the first hydrogen-containing stream 34 can comprise hydrogen and methane, and wherein a separate methane steam is not recovered. In such aspects, a purge can be taken off the first hydrogen-containing stream 34 (e.g., prior to recycling stream 34 to reactor 100), for example to avoid build-up of methane in the reactor 100.

The first separation unit 200 can comprise any suitable separation unit that is configured to separate the hydrogenolysis product stream 20 into the butane stream 30, the first hydrogen-containing stream 34, the optional methane stream 36, and the $C_2$ to $C_3$ gas stream 38. For example, the first separation unit 200 can employ distillation, cryogenic distillation, extractive distillation, selective adsorption, selective absorption, and the like, or combinations thereof. The first separation unit 200 can comprise a distillation column, a cryogenic distillation column, a trayed and/or packed separation column, a compressor, a heat exchanger, a cooling tower, a pressure swing adsorption (PSA) unit, etc.

Generally, hydrogen can be recovered by using any suitable methodology, such as PSA, membrane separation, cryogenic separation, etc. In some aspects, hydrogen (e.g., high-purity hydrogen) can be recovered by using a PSA process which is based on a physical binding of gas molecules to adsorbent material, wherein forces acting between gas molecules and adsorbent material depend on the gas component, type of adsorbent material, partial pressure of the gas component and operating temperature. The separation effect is based on differences in binding forces to the adsorbent material. Highly volatile components with low polarity, such as hydrogen, are practically non-adsorbable, as opposed to molecules such as hydrocarbons, nitrogen, carbon monoxide, carbon dioxide, water vapor, etc., and as such high purity hydrogen can be recovered.

Individual hydrocarbons or hydrocarbon fractions can be usually recovered by fractionation processes that can employ a variety of columns, such as a cryogenic distillation column configuration comprising a demethanizer, a deethanizer, a depropanizer, etc.

In some aspects, the butane stream 30 can be fed to the dehydrogenation reactor 300, for example as depicted in FIG. 1, and as will be described in more detail later herein.

In aspects where the butane stream 30 comprises n-butane, the n-butane can be separated from the butane stream 30 to yield n-butane stream 32, for example via cryogenic distillation. The n-butane stream 32 can be recycled to the hydrogenolysis reactor 100.

In some aspects, the first separation unit 200 (as depicted in FIG. 2) can be configured to separate the hydrogenolysis product stream 20 into a first i-butane stream 31, the n-butane stream 32, the first hydrogen-containing stream 34, the optional methane stream 36, and the $C_2$ to $C_3$ gas stream 38. In such aspects, the first i-butane stream 31 can be fed to the dehydrogenation reactor 300, for example as depicted in FIG. 2, and as will be described in more detail later herein; and the n-butane stream 32 can be optionally recycled to the hydrogenolysis reactor 100.

In an aspect, at least a portion 34a of the first hydrogen-containing stream 34 can be recycled to the hydrogenolysis reactor 100.

In an aspect, the $C_2$ to $C_3$ gas stream 38 can be characterized by an ethane to propane weight ratio of equal to or greater than about 2:1, alternatively equal to or greater than about 3:1, alternatively equal to or greater than about 4:1, alternatively equal to or greater than about 5:1, alternatively equal to or greater than about 6:1, or alternatively equal to or greater than about 7:1.

In some aspects, at least a portion of the $C_2$ to $C_3$ gas stream 38 can be fed to a gas steam cracker furnace to produce a steam cracker product stream, wherein the steam cracker product stream comprises olefins, wherein an amount of olefins in the steam cracker product stream is greater than an amount of olefins in the $C_2$ to $C_3$ gas stream 38, and wherein the olefins comprise ethylene and propylene. The olefins can comprise ethylene and propylene in a weight ratio of ethylene to propylene of equal to or greater than about 4:1, alternatively equal to or greater than about 5:1, alternatively equal to or greater than about 6:1, or alternatively equal to or greater than about 7:1. Steam cracking of ethane and/or propane is described in more detail in U.S. Provisional Patent Application No. 62/733,284, filed Sep. 19, 2018, which is incorporated by reference herein in its entirety.

In an aspect, the process for producing isooctane as disclosed herein can comprise feeding at least a portion of the butane stream 30 to the dehydrogenation reactor 300 (as depicted in FIG. 1) to produce a dehydrogenation product stream 40, wherein the dehydrogenation reactor 300 comprises a dehydrogenation catalyst, and wherein the dehydrogenation product stream 40 comprises hydrogen, i-butane, and isobutylene. In aspects where the butane stream 30 comprises n-butane, the dehydrogenation product stream 40 can further comprise 1-butene, 2-butene, butadiene, or combinations thereof.

In aspects where the n-butane is recovered from the butane stream (e.g., in the first separation unit 200), the process for producing isooctane as disclosed herein can comprise feeding at least a portion of the first i-butane stream 31 to the dehydrogenation reactor 300 (as depicted in FIG. 2) to produce the dehydrogenation product stream 40; wherein the dehydrogenation product stream 40 comprises hydrogen, i-butane, and isobutylene.

In an aspect, the dehydrogenation of the butane stream 30 and/or the first i-butane stream 31 can be performed by using any suitable methodology. For example, the dehydrogenation of the butane stream 30 and/or the first i-butane stream 31 can be performed via a CATOFIN® dehydrogenation process; although any other suitable dehydrogenation process can be used for the dehydrogenation of the butane stream 30 and/or the first i-butane stream 31. CATOFIN® dehydrogenation process is a process of Lummus Technology for dehydrogenation of i-butane, n-butane, propane, etc. for the production or isobutylene, n-butenes, propylene, etc., respectively. The CATOFIN® dehydrogenation process uses fixed-bed reactors with a catalyst and operating conditions that are selected to optimize conversion and selectivity. For example, the overall selectivity of i-butene dehydrogenation to isobutylene in a CATOFIN® dehydrogenation process can be greater than 90%.

In an aspect, the dehydrogenation reactor 300 can comprise any suitable dehydrogenation reactor, such as a continuous flow fixed bed reactor.

The dehydrogenation reactor 300 can comprise any suitable dehydrogenation catalyst, such as a chromia-alumina $(Cr_2O_3/Al_2O_3)$ catalyst.

In an aspect, the process for producing isooctane as disclosed herein can comprise feeding at least a portion of the dehydrogenation product stream 40 to the oligomerization unit 400 (as depicted in FIG. 1) to an isooctene stream 50. Isooctene stream 50 is then fed with a hydrogen 90 to the hydrogenation unit 500 to produce an isooctane steam 70. Unreacted hydrogen 80 may be recycled to the hydrogenation unit 500. While the present invention is not limited to any specific catalyst for the oligomerization of isobutylene to isooctene, preferably the catalyst is an acidic or slightly acidic catalyst. Non-limiting examples include zeolites, including Beta, FER, MOR, MFI, and Y. Non-limiting examples of acidic aluminas, including phosphated-Alumina, Ni—Al2O3, NiSO4-Al2O3. Additional examples include ion-exchange resins, including Amberlyst, Tulsion, and Amberlite. The hydrogenation unit 500 can used any suitable hydrogenation catalyst, non-limiting examples include Ni supported on alumina or other suitable support, or Pt and/or Pd supported on alumina or other suitable support.

In aspects where the dehydrogenation product stream 40 comprises hydrocarbons other than isobutylene, the unreacted isobutylene stream 51 can comprise at least a portion of such hydrocarbons, e.g., i-butane, n-butane, 1-butene, 2-butene, butadiene, or combinations thereof. In some aspects, at least a portion 51a of the unreacted isobutylene stream 51 can be recycled to the oligomerization unit 400. In an aspect, isobutylene can be separated from the unreacted isobutylene stream 51, for example via cryogenic distillation, wherein the separated isobutylene can be recycled to the oligomerization unit 400.

In aspects where the dehydrogenation product stream 40 comprises hydrocarbons other than isobutylene, the dehydrogenation product stream 40 can be subjected to a separation step to recover isobutylene, wherein at least a portion of the recovered isobutylene (e.g., isobutylene stream 45) can be fed to the oligomerization unit 400, for example as depicted in FIG. 2, and as will be described in more detail later herein. In such aspects, an unreacted isobutylene stream 51 can be recovered from the oligomerization unit 400, wherein at least a portion 51a of the unreacted isobutylene stream 51 can be recycled to the oligomerization unit 400. In some cases, stream 51 and 51a can be the same stream.

In an aspect, at least a portion 52a of the unreacted hydrogen stream 52 can be recycled to the oligomerization unit 400.

In an aspect, the oligomerization of the dehydrogenation product stream 40 and/or the isobutylene stream 45 with hydrogen can be performed by using any suitable methodology. For example, the oligomerization of the dehydrogenation product stream 40 and/or the isobutylene stream 45 with hydrogen can be performed via NEXOCTANE® of Neste which involves isobutylene dimerization the liquid phase in adiabatic reactors over fixed beds of acidic ion-exchange resin catalyst followed by hydrogenation.

In an aspect, the oligomerization unit 400 can comprise any suitable oligomerization reactor configuration.

In an aspect, the process for producing isooctane as disclosed herein can comprise optionally separating at least a portion of the dehydrogenation product stream 40 in the second separation unit 350 (as depicted in FIG. 2) into a second hydrogen-containing stream 44, a second i-butane stream 41, and the isobutylene stream 45. In some aspects, the second hydrogen-containing stream 44 can further comprise fairly low amounts of hydrocarbons (e.g., i-butane, isobutylene, etc.) owing to less than 100% separation efficiency in the second separation unit 350.

The second separation unit 350 can comprise any suitable separation unit that is configured to separate the dehydrogenation product stream 40 into the second hydrogen-containing stream 44, the second i-butane stream 41, and the isobutylene stream 45. For example, the second separation unit 350 can employ distillation, cryogenic distillation, extractive distillation, selective adsorption, selective absorption, and the like, or combinations thereof. The second separation unit 350 can comprise a distillation column, a cryogenic distillation column, a trayed and/or packed separation column, a compressor, a heat exchanger, a cooling tower, a pressure swing adsorption (PSA) unit, etc.

In an aspect, the process for producing isooctane as disclosed herein can comprise feeding at least a portion of the isobutylene stream 45 to the oligomerization unit 400.

In an aspect, at least a portion 44a of the second hydrogen-containing stream 44 can be recycled to the hydrogenolysis reactor 100.

In an aspect, at least a portion 41a of the second i-butane stream 41 can be recycled to the dehydrogenation reactor 300.

In an aspect, the process for producing isooctane as disclosed herein, and for example as illustrated in FIG. 2, can comprise (a) introducing a butane feed stream 10 and hydrogen 15 to a hydrogenolysis reactor 100 to produce a hydrogenolysis product stream 20, wherein the hydrogenolysis reactor 100 comprises a hydrogenolysis bimetallic supported catalyst, wherein the hydrogenolysis bimetallic supported catalyst comprises Pt and Ir supported on ZSM-5, wherein the hydrogenolysis reactor 100 is characterized by a temperature of less than about 330° C., wherein the hydrogenolysis reactor 100 is characterized by an i-butane conversion of less than about 25%, wherein the butane feed stream 10 comprises n-butane and i-butane, wherein the butane feed stream 10 is characterized by a mole ratio of n-butane to i-butane of equal to or greater than about 1:1, and wherein the hydrogenolysis product stream 20 comprises hydrogen, methane, ethane, propane, and i-butane; (b) separating at least a portion of the hydrogenolysis product stream 20 in a first separation unit 200 into a first hydrogen-containing stream 34, an optional methane stream 36, a $C_2$ to $C_3$ gas stream 38, a first i-butane stream 31, and optionally an n-butane stream 32, wherein the $C_2$ to $C_3$ gas stream 38 comprises ethane and propane; (c) feeding at least a portion of the i-butane stream 31 to a dehydrogenation reactor 300 to produce a dehydrogenation product stream 40, wherein the dehydrogenation reactor 300 comprises a dehydrogenation catalyst (e.g., a chromia-alumina catalyst), and wherein the dehydrogenation product stream 40 comprises hydrogen, i-butane, and isobutylene; (d) separating at least a portion of the dehydrogenation product stream 40 in a second separation unit 350 into a second hydrogen-containing stream 44, a second i-butane stream 41, and an isobutylene stream 45; (e) feeding at least a portion of the isobutylene stream 45 to an oligomerization unit 400 to produce an unreacted isobutylene stream 51, and an isooctene stream 50; (f) optionally recycling at least a portion 51a of the unreacted isobutylene stream 51 to the oligomerization unit; (g) optionally recycling at least a portion 41a of the second i-butane stream 41 to the dehydrogenation reactor 300; (h) optionally recycling at least a portion 34a of the first hydrogen-containing stream 34 and/or at least a portion 44a of the second hydrogen-containing stream 44 to the hydrogenolysis reactor 100; and (i) optionally feeding at least a portion of the $C_2$ to $C_3$ gas stream 38 to a gas steam cracker furnace to produce a steam cracker product stream, wherein the steam cracker product stream comprises olefins, wherein an amount of olefins in the steam cracker product stream is greater than an amount of olefins in the $C_2$ to $C_3$ gas stream 38, and wherein the olefins comprise ethylene and propylene in a weight ratio of ethylene to propylene of equal to or greater than about 5:1.

In some aspects, a process for producing isooctane as disclosed herein can advantageously display improvements in one or more method characteristics when compared to an otherwise similar process that lacks a step of introducing a butane feed stream and hydrogen to a hydrogenolysis reactor. Conventionally, field-grade butane streams can be subjected to isomerization for conversion of n-butane to i-butane; however, such conversion is not complete (because it is equilibrium-limited). The process for producing isooctane as disclosed herein can advantageously provide for an increased conversion of n-butane in the hydrogenolysis reactor, thus reducing the separation units load and recycle stream volumes.

In an aspect, a process for producing isooctane as disclosed herein can advantageously provide for a reactive separation of field-grade butane streams, wherein the n-butane can be converted in the hydrogenolysis reactor, and wherein the i-butane can be recovered and dehydrogenated to isobutylene, thereby providing for a more efficient method of separating i-butane from n-butane, wherein the products of n-butane conversion can be further subjected to steam cracking to produce ethylene. Hydrogenolysis as disclosed herein can provide for an enhanced amount of ethane, as compared to the amount of ethane produced from a similar feed stream subjected to hydrocracking. Additional advantages of the process for producing isooctane as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

Selective hydrogenolysis of butanes was investigated in the presence of multiple monometallic catalysts (e.g., hydrogenolysis monometallic supported catalysts) and bimetallic catalysts (e.g., hydrogenolysis bimetallic supported catalysts). The data presented below are experimental data associated with the bimetallic catalyst (Ir,Pt/ZSM-5) comprising 0.3 wt. % Ir and 0.3 wt. % Pt supported on ZSM-5, wherein the ZSM-5 support was characterized by a weight ratio of silica to alumina (SAR or $SiO_2/Al_2O_3$) of 280. The bimetallic catalyst (Ir,Pt/ZSM-5) was employed in experiments run at two different conditions. The results of these experiments demonstrated that when a catalyst (e.g., hydrogenolysis catalyst) is subjected to a reaction (e.g., hydrogenolysis) under a very specific set of conditions, a reactive separation can be achieved between n-butane and isobutane. The data are displayed in Table 1.

TABLE 1

Example of selective hydrogenolysis reaction for integration with isooctane production:

| | | Temp (° C.) | Pressure (psig) | WHSV (/hr) | H2/C4 (mole ratio) | n-C4 Conversion (%) | i-C4 Conversion (%) | Methane Selectivity (mole %) | Ethane Selectivity (mole %) | Propane Selectivity (mole %) |
|---|---|---|---|---|---|---|---|---|---|---|
| Comparative Example A (without hydrogenolysis reaction) | Without selective hydrogenolysis, the mixed butane (n/i-C4) would have to undergo isomerization and a separation step to have a pure isobutane stream to feed to a dehydrogenation unit within a isooctane production complex. | | | | | | | | | |
| Comparative Example B | 0.3 wt. % Ir-0.3 wt. % Pt/ZSM-5 | 350 | 100 | 4/hr | 2.5 | 100% | 100% | 81% | 19% | 0% |
| Comparative Example C | 0.3 wt. % Ir-0.3 wt. % Pt/ZSM-5 | 300 | 100 | 6/hr | 5 | 24% | 3% | 13% | 75% | 12% |
| Selective hydrogenolysis/Reactive separation | 0.3 wt. % Ir-0.3 wt. % Pt/ZSM-5 | 300 | 100 | 4/hr | 2.5 | 99% | 13% | 19% | 74% | 8% |

Further, a comparative experiment was run (Comparative Example B), and the resulting data are also displayed in Table 1. In the comparative experiment run at a temperature of 350° C., one can see that both the n-butane and isobutane are fully converted. Another comparative experiment (Comparative Example C) shows that at high WHSV and $H_2/C_4$ mole ratio, n-butane is not consumed in a sufficient amount to allow for a reactive separation from isobutane.

However, it was unexpectedly found that by adjusting the temperature to 300° C., and with a WHSV of 4 $h^{-1}$ and a $H_2/C_4$ mole ratio of 2.5, the conversion of n-butane is still nearly complete (99-100%), however, the conversion of isobutane drops significantly (10-15%). Due to this phenomena from the selective hydrogenolysis/reactive separation experimental run, the product stream is then composed of gases, i.e., methane, ethane, propane, and isobutane. The isobutane can be easily separated from this mixture. Since there is no n-butane present, the need for a conventional isomerization and separation unit for n/i-C4 is not necessary. Thus, the isobutane can be directly fed into a conventional dehydrogenation unit to form isobutylene, which can then be oligomerized to form the product isooctane.

A further comparative example (Comparative Example A) is the case without performing the selective hydrogenolysis reaction, where in Comparative Example A the n-butane and isobutane would have to be separated using an isomerization unit to convert a portion of the n-butane into isobutane followed by a boiling point separation column to separate the n-butane from isobutane. The n-butane would be recycled to extinction in the isomerization unit and the isobutane would go on to a dehydrogenation unit and isooctane production. By using the selective hydrogenolysis/reactive separation experimental run in Table 1, the conventional isomerization and separation steps, which are very energy intensive, can be avoided.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process comprising:
    (a) introducing a butane feed stream and hydrogen to a hydrogenolysis reactor to produce a hydrogenolysis product stream, wherein the hydrogenolysis reactor comprises a hydrogenolysis catalyst, wherein the butane feed stream comprises n-butane and i-butane, wherein said catalyst having higher selectivity towards hydrogenolysis of n-butane compared to hydrogenolysis of i-butane, wherein the hydrogenolysis product stream comprises hydrogen, methane, ethane, propane, i-butane, and n-butane, and further wherein said hydrogenolysis product stream has a higher i-butane: n-butane ratio than the butane feed stream;

(b) separating at least a portion of the hydrogenolysis product stream in a first separation unit into a first hydrogen-containing stream, a stream rich in methane, ethane and propane, and a butane stream, wherein the butane stream comprises i-butane and n-butane;

(c) feeding at least a portion of the butane stream to a dehydrogenation reactor to produce a dehydrogenation product stream, wherein the dehydrogenation reactor comprises a dehydrogenation catalyst, and wherein the dehydrogenation product stream comprises hydrogen, i-butane, isobutylene, n-butane, 1-butene, and 2-butene, (d) feeding at least a portion of the dehydrogenation product stream to an oligomerization unit to produce a product stream comprising isooctene; and, (e) feeding at least a portion of the product stream comprising isooctene to a hydrogenation unit to produce isooctane.

2. The process of claim 1, wherein the n-butane is present in the butane feed stream in an amount of equal to or greater than about 50 mol %.

3. The process of claim 1, further comprising recycling at least a portion of the first hydrogen-containing stream to the hydrogenolysis reactor.

4. The process of claim 1, wherein said portion of the dehydrogenation product stream comprises the dehydrogenation product stream from step (c) after the removal of at least a portion of the hydrogen to form a second hydrogen-containing stream.

5. The process of claim 4, further comprising recycling at least a portion of the second hydrogen-containing stream to the hydrogenolysis reactor.

6. The process of claim 1, wherein the hydrogenolysis reactor is characterized by a temperature of from about 200° C. to about 350° C.; a pressure of from about 0 psig to about 300 psig; a hydrocarbon-based weight hourly space velocity (WHSV) of from about 0.1 h-1 to about 15 h-1; and a hydrogen to C4 hydrocarbons molar ratio of from about 1:1 to about 10:1.

7. The process of claim 1, wherein the hydrogenolysis catalyst comprises a hydrogenolysis monometallic supported catalyst and/or a hydrogenolysis bimetallic supported catalyst; wherein the hydrogenolysis monometallic supported catalyst comprises a zeolite-supported monometallic catalyst and/or an alumina-supported monometallic catalyst; wherein the hydrogenolysis bimetallic supported catalyst comprises a zeolite-supported bimetallic catalyst and/or an alumina-supported bimetallic catalyst; wherein the hydrogenolysis bimetallic supported catalyst comprises a first metal and a second metal, wherein the first metal and the second metal are different; wherein the hydrogenolysis monometallic supported catalyst comprises a third metal; wherein the third metal is the same as or different from the first metal and/or the second metal; wherein the first metal, the second metal, and the third metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co); wherein the support comprises alumina and/or a zeolite; wherein the zeolite is selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof; and wherein the support optionally comprises a binder comprising alumina, titania, silica, or combinations thereof.

8. The process of claim 1, wherein the hydrogenolysis catalyst comprises Pt and Ir supported on ZSM-5.

9. The process of claim 1, further comprising recycling at least a portion of the dehydrogenation product stream to the dehydrogenation reactor.

10. The process of claim 1, wherein step (b) of separating at least a portion of the hydrogenolysis product stream in a first separation unit further comprises separating at least a portion of the n-butane from the hydrogenolysis product stream.

11. The process of claim 9, further comprising recycling at least a portion of the separated n-butane to the hydrogenolysis reactor.

12. The process of claim 1, wherein the hydrogenolysis reactor is characterized by an i-butane conversion of less than about 25%.

13. The process of claim 1, wherein the hydrogenolysis reactor is characterized by a n-butane conversion of equal to or greater than about 70%.

14. The process of claim 1, further comprising feeding at least a portion of the stream rich in methane, ethane and propane to a gas steam cracker furnace to produce a steam cracker product stream, wherein the steam cracker product stream comprises ethylene and propylene.

15. The process of claim 1, wherein an ethane to propane weight ratio in the stream rich in methane, ethane and propane is equal to or greater than about 2:1.

16. The process of claim 1, wherein the step of feeding at least a portion of the dehydrogenation product stream to an oligomerization unit comprises feeding at least a portion of the dehydrogenation product stream to an oligomerization unit having an acidic or slightly acidic oligomerization catalyst.

17. A process for producing isooctane comprising:

(a) introducing a butane feed stream and hydrogen to a hydrogenolysis reactor to produce a hydrogenolysis product stream, wherein the hydrogenolysis reactor comprises a hydrogenolysis bimetallic supported catalyst, wherein the hydrogenolysis bimetallic supported catalyst comprises Pt and Ir supported on ZSM-5, wherein the hydrogenolysis reactor is characterized by a temperature of less than about 350°C., wherein the hydrogenolysis reactor is characterized by an i-butane conversion of less than about 25%, wherein the butane feed stream comprises n-butane and i-butane, wherein the butane feed stream is characterized by a mole ratio of n-butane to i-butane of equal to or greater than about 1:1, and wherein the hydrogenolysis product stream comprises hydrogen, methane, ethane, propane, i-butane, and n-butane;

(b) separating at least a portion of the hydrogenolysis product stream in a first separation unit into a first hydrogen-containing stream, a stream rich in methane, ethane and propane, and a first i-butane stream;

(c) feeding at least a portion of the first i-butane stream to a dehydrogenation reactor to produce a dehydrogenation product stream, wherein the dehydrogenation reactor comprises a dehydrogenation catalyst, and wherein the dehydrogenation product stream comprises hydrogen, i-butane, and isobutylene;

(d) separating at least a portion of the dehydrogenation product stream in a second separation unit into a second hydrogen-containing stream, a second i-butane stream, and an isobutylene stream; (e) feeding at least a portion of the isobutylene stream and hydrogen to an oligomerization unit to produce an isooctene-containing stream; and (f) feeding at least a portion of the isooctene-containing stream to a hydrogenation unit to produce isooctane.

18. The process of claim 17, further comprising feeding at least a portion of the stream rich in methane, ethane and propane to a gas steam cracker furnace to produce a steam cracker product stream, wherein the steam cracker product stream comprises olefins.

19. The process of claim 18, wherein the steam cracker product stream comprises ethylene and propylene in a weight ratio of ethylene to propylene of equal to or greater than about 2:1.

20. The process of claim 17, further comprising recycling at least a portion of the first hydrogen-containing stream and/or at least a portion of the second hydrogen-containing stream to the hydrogenolysis reactor.

21. The process of claim 17, further comprising recycling at least a portion of the second i-butane stream to the dehydrogenation reactor.

\* \* \* \* \*